(12) United States Patent
Han

(10) Patent No.: US 7,093,603 B2
(45) Date of Patent: Aug. 22, 2006

(54) HAND PIECE FOR REMOVING THE CALLUSES OF THE SKIN

(75) Inventor: Jong Sam Han, Incheon (KR)

(73) Assignee: Oxyvac Medical Instrument Co., Ltd., Kyunggi-Do (KR)

( * ) Notice: Subject to any disclaimer, the term of this patent is extended or adjusted under 35 U.S.C. 154(b) by 297 days.

(21) Appl. No.: 10/242,242

(22) Filed: Sep. 12, 2002

(65) Prior Publication Data

US 2004/0016438 A1    Jan. 29, 2004

(30) Foreign Application Priority Data

Jul. 26, 2002    (KR) ............................... 2002-44068

(51) Int. Cl.
*A45D 29/18* (2006.01)

(52) U.S. Cl. ..................... 132/76.4; 132/75.4

(58) Field of Classification Search ............... 132/76.6, 132/73.5, 73.6, 75.3, 75.4, 75.5, 75.6, 76.4; 30/526, 327; 604/22; 606/159, 171

See application file for complete search history.

(56) References Cited

U.S. PATENT DOCUMENTS

| | | | | |
|---|---|---|---|---|
| 1,106,894 A | * | 8/1914 | Samphere | 132/75.4 |
| 1,682,475 A | * | 8/1928 | Blomquist | 132/75.8 |
| 2,460,522 A | * | 2/1949 | Miller | 132/75.4 |
| 2,746,461 A | * | 5/1956 | Bocchino | 132/75.4 |
| 3,600,803 A | * | 8/1971 | Nachsi | 132/75.4 |
| 4,643,207 A | * | 2/1987 | Grahame | 132/73.6 |
| 5,106,364 A | * | 4/1992 | Hayafuji et al. | 604/22 |
| 5,476,473 A | * | 12/1995 | Heckele | 606/171 |
| 5,507,760 A | * | 4/1996 | Wynne et al. | 606/159 |
| 5,687,485 A | * | 11/1997 | Shurtleff et al. | 30/526 |
| 5,911,701 A | * | 6/1999 | Miller et al. | 604/22 |
| 6,818,001 B1 | * | 11/2004 | Wulfman et al. | 606/159 |

* cited by examiner

*Primary Examiner*—John J. Wilson
*Assistant Examiner*—Robyn Doan
(74) *Attorney, Agent, or Firm*—Birch, Stewart, Kolasch & Birch, LLP

(57) ABSTRACT

A skin treating implement, a callus removing hand piece, is used to remove skin calluses. The hand piece is connected to a vacuum suction device. The hand piece has a main body that is bent at a certain degree for greater usability. Below the bend, there is a detachable mount for a cutter with a desired shape. In the upper part of the main body, connectors with nipples can be mounted to be inserted into a suction tube connectable to a vacuum device to ensure compatibility with the suction device. Because the lower portion of the main body of the hand piece is bent, it facilitates removing calluses and permits mounting and unmounting cutters permitting a choice of cutter appropriate for the king of callus to be removed. Connectors with nipples of suitable diameters permit use of suction tubes of existing high-priced vacuum suction devices to make the callus removing hand piece economical. A disposable sheet fixer injection molded with synthetic resins is attachable to the cutter. Use of the hand piece can minimize incidence of skin diseases and efficiently remove calluses.

6 Claims, 6 Drawing Sheets

HAND PIECE FOR REMOVING THE CALLUSES OF THE SKIN

BACKGROUND OF THE INVENTION

1. Field of the Invention

This invention concerns the callus-removing hand piece used to remove calluses of the skin which directly causes the human skin to age. More specifically, in configuring this hand piece connected to the vacuum suction device, the lower part of the main body of the above mentioned hand piece is bent at a certain degree for greater usability. Below the bend there is a detachable cutter so that you can mount a cutter with a desirable shape. In the upper part of the main body, connectors with nipples can be mounted so that they are inserted into the suction tube near the already equipped vacuum suction device to ensure compatibility with the vacuum suction device.

As the lower part of the main body of the hand piece is bent, it is easy to remove calluses, and possible to mount and unmount cutters. So you can choose a cutter appropriate for the kind of callus you want to remove.

Besides, as you can choose connectors with nipples of the right diameter for the suction tube, you can use your existing high-priced vacuum suction device. So it is very economical.

Another application of this invention is that you can attach a disposable sheet fixer injection-molded with synthetic resins to the cutter. Therefore it will be possible to minimize incidence of skin diseases and efficiently remove calluses.

2. Background of the Related Art

In general, the facial callus, enlarged pores, pimple scars, striae distensae, Keratosis Pilaris, small scars, drab and rough skin, skin damaged due to sunlight can cause not only cosmetic problems unless treated properly, but also many skin troubles like skin diseases, so they are considered as serious cosmetic problems.

Accordingly, people tried to solve the above problems by using the usual cleaners or makeup remover (e.g. cold cream), but these solutions were not good enough, and recently callus removers have been developed to remove calluses.

The above-mentioned callus removers are connected to the suction tube of the vacuum suction device to remove aged calluses on the skin surface. Crystal callus remover and diamond callus removers are used to remove calluses of the skin.

On the other hand, each part of the above crystal callus remover is integrated into the main body, and there are two passages inside the main body. Through one passage (central passage) crystal powder is sprayed to contact the skin and cause friction so that calluses are removed, whereas through the other passage (suction hole) both the removed calluses and crystal powder are sucked out. As the crystal powder rubs against the skin to remove calluses, this method is noticeably inefficient, and if carelessness leads to a gap between the callus remover and the skin when calluses are removed, the crystal powder and the removed calluses may not be sucked into the suction hole, and instead they may be sprayed onto the operator or the person whose calluses are being removed, thereby sticking to the eye, hair or clothes, and inhaled through the respiratory organ. So it is unsanitary.

Moreover, as it is an all-in-one type, you will need to have a set of callus removers of various shapes, and after you use it on one person, you will need to wash and sterilize them before using them again to remove another person's calluses. So you used to need several sets of callus removers, making them uneconomical and unsanitary.

On the other hand, the diamond callus remover makes up for the weaknesses of the above-mentioned crystal callus remover. Inside the main body is a passage, and in the lower part that comes into contact with the skin is a cutting surface made of diamond with minute embossments.

In other words, the diamond callus remover has a vacuum passage inside, and the top part has the nipple that connects to the suction tube next to the vacuum suction device, and the cutter in the bottom has a cutting surface made of diamond. While the diamond callus remover is in use, the nipple in the top connects to the suction tube next to the vacuum suction device, and the cutting surface in the bottom comes into contact with the skin. The cutting surface removes skin calluses, and the removed calluses are sucked into the vacuum suction device through the internal passage.

However, as the diamond callus remover also consists of a set of multiple callus removers of various shapes, the user must purchase several sets of callus removers, making it uneconomical. Besides, as it is straight like a stick, when you hold it in your hand to remove calluses, you will need to rub against the skin to remove calluses while holding the callus remover at right angles to the skin, making it inconvenient to use.

SUMMARY OF THE INVENTION

The objective of this invention is to solve the above-mentioned problems. In configuring the hand piece that connects to the vacuum suction device, the lower part of the main body, which is the hand piece, is bent at a certain angle for improved usability, and below the bend the cutter is detachable so that you can replace the cutter with one of a shape you desire. In the top part of the main body there is a detachable suction connector with different diameters so that the callus-removing hand piece can be used also with the suction tubes next to the existing vacuum suction device of different diameters.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings;

FIG. 4b is the assembled cross section of FIG. 4a;

FIG. 5b is the assembled cross section of FIG. 5a; and

(Description of numeral reference for parts)

| | | |
|---|---|---|
| 1 hand piece | 10 main body | |
| 20 mount | 22 surrounding groove | |
| 24 ring | 30 fastening part | |
| 32 holder | 34 screw thread | |
| 40 connector | 42 fastener | |
| 44 nipple | 60 cutter | |
| 63 cutting surface | 64 suction hole | 80 sheet fixer |
| | | 84 sheet insertion groove |
| 90 diamond sheet | 100 vacuum suction device | |
| 102 suction tube | | |

DETAILED DESCRIPTION OF THE INVENTION

Reference will now be made in detail to the preferred embodiments of the present invention, examples of which are illustrated in the accompanying drawings.

Figure 1:
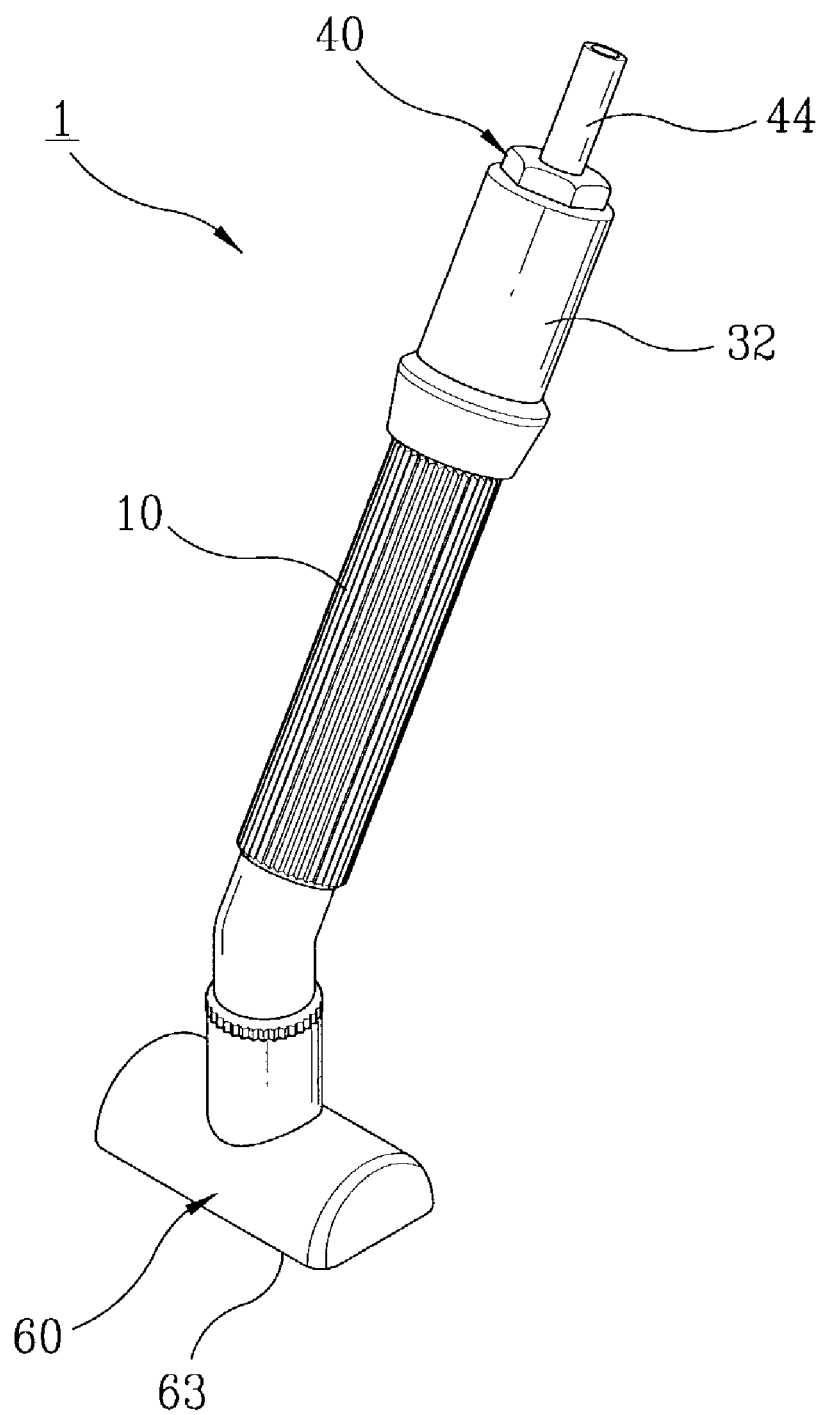
FIG. 1 is the perspective view of this invention being properly used.
Figure 2:
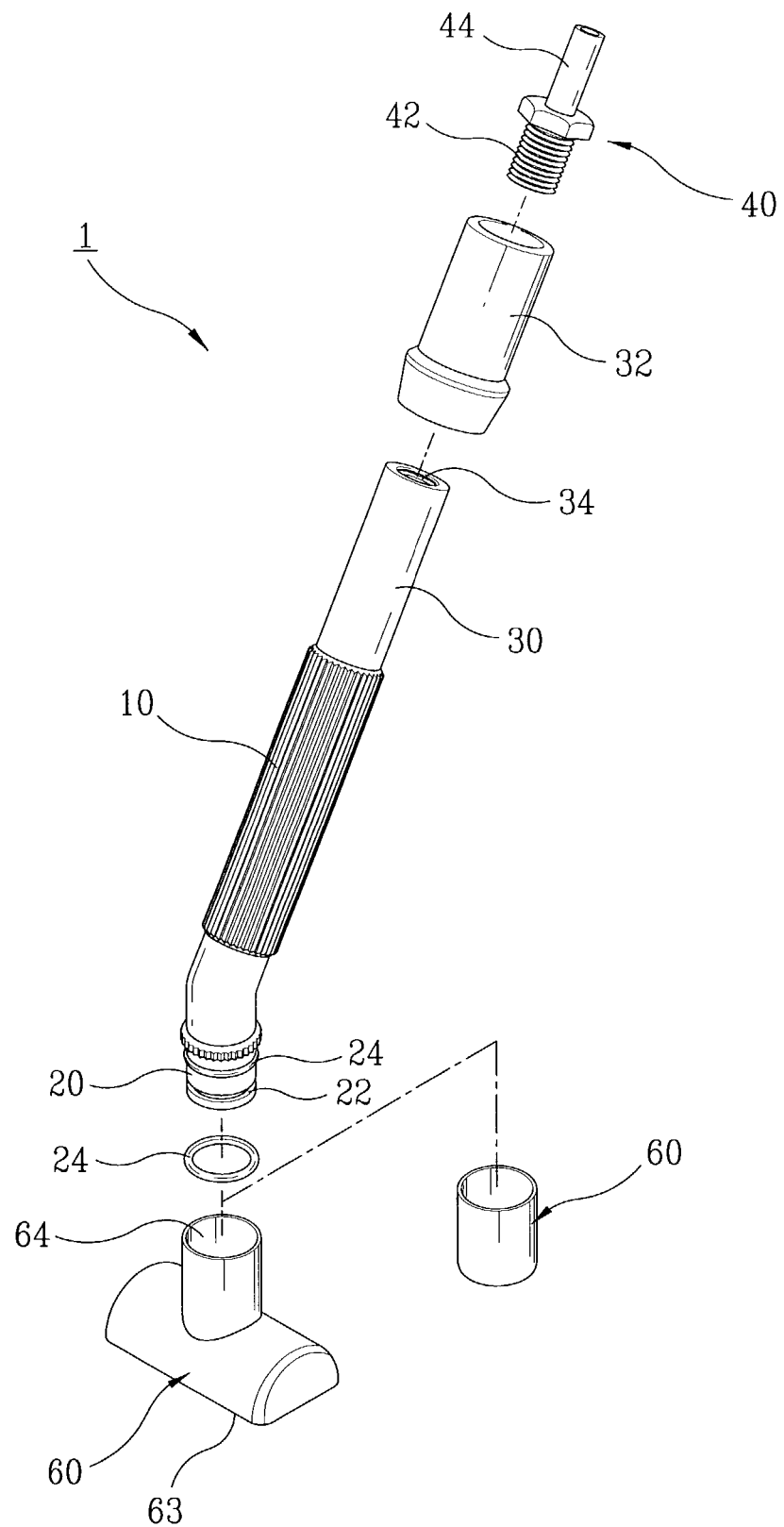
FIG. 2 is the exploded perspective view of the hand piece of this invention being properly used.
Figure 3:
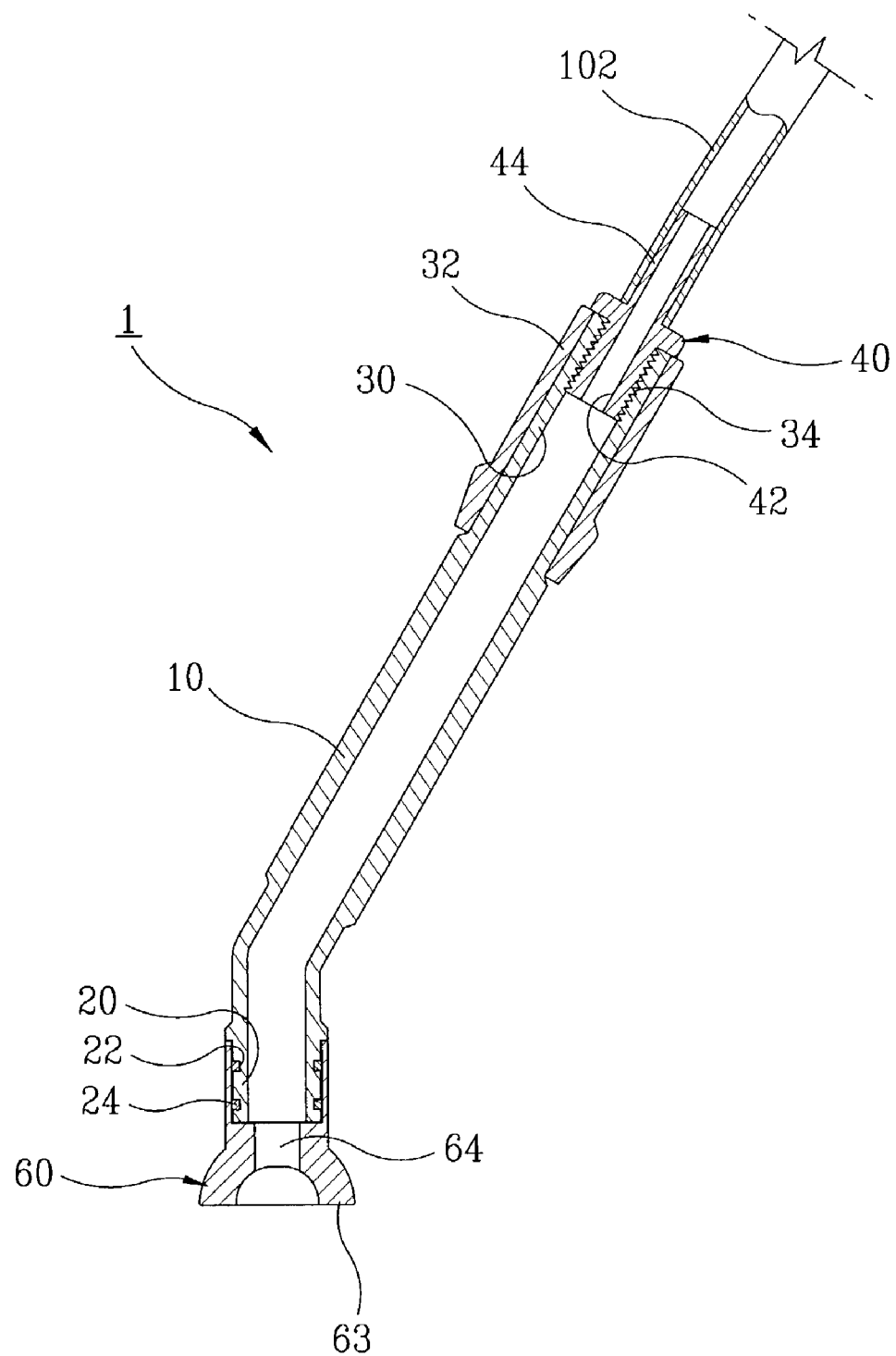
FIG. 3 is the assembled cross section of this invention being properly sued.
Figure 4A:
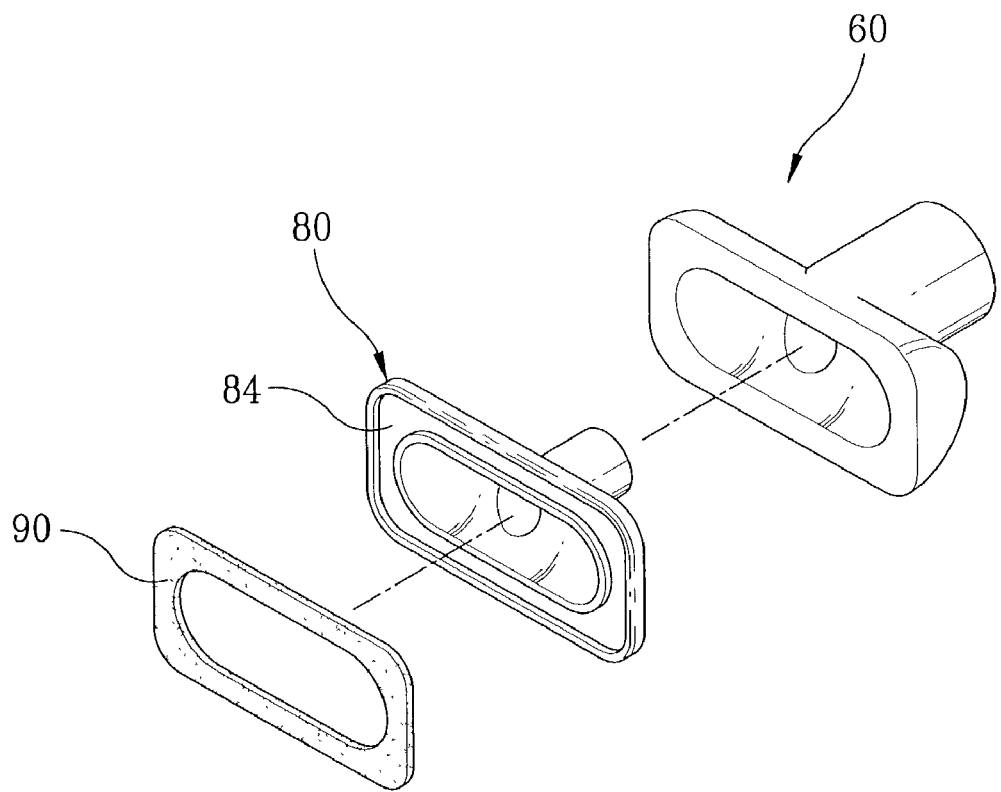
FIG. 4a is the exploded perspective view of the cutter being used another way.
Figure 4B:
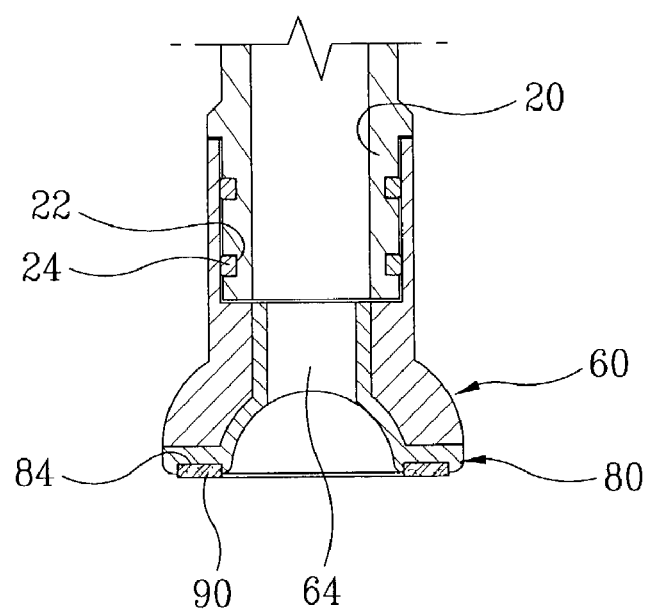
Figure 5A:
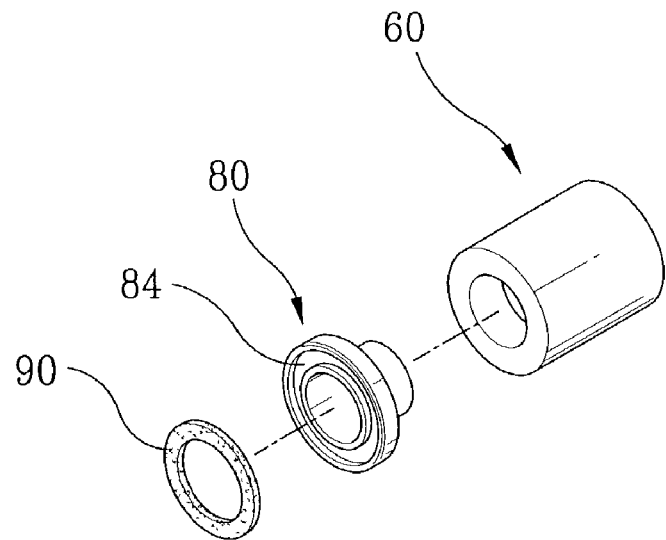
FIG. 5a is the exploded perspective view of the cutter of this invention being used another way.
Figure 5B:
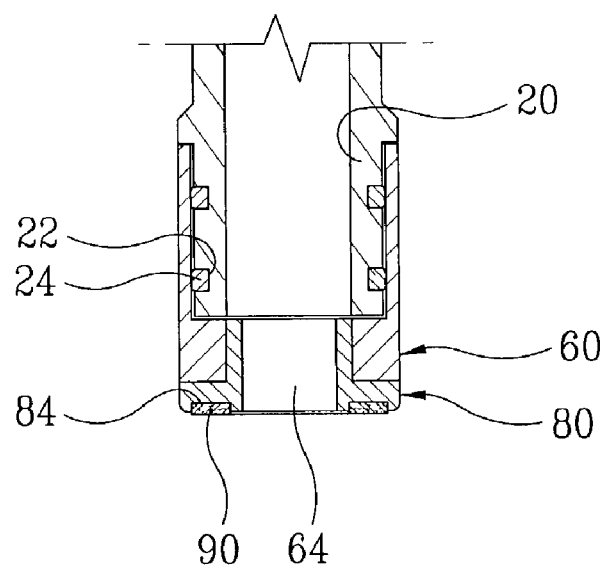
Figure 6:
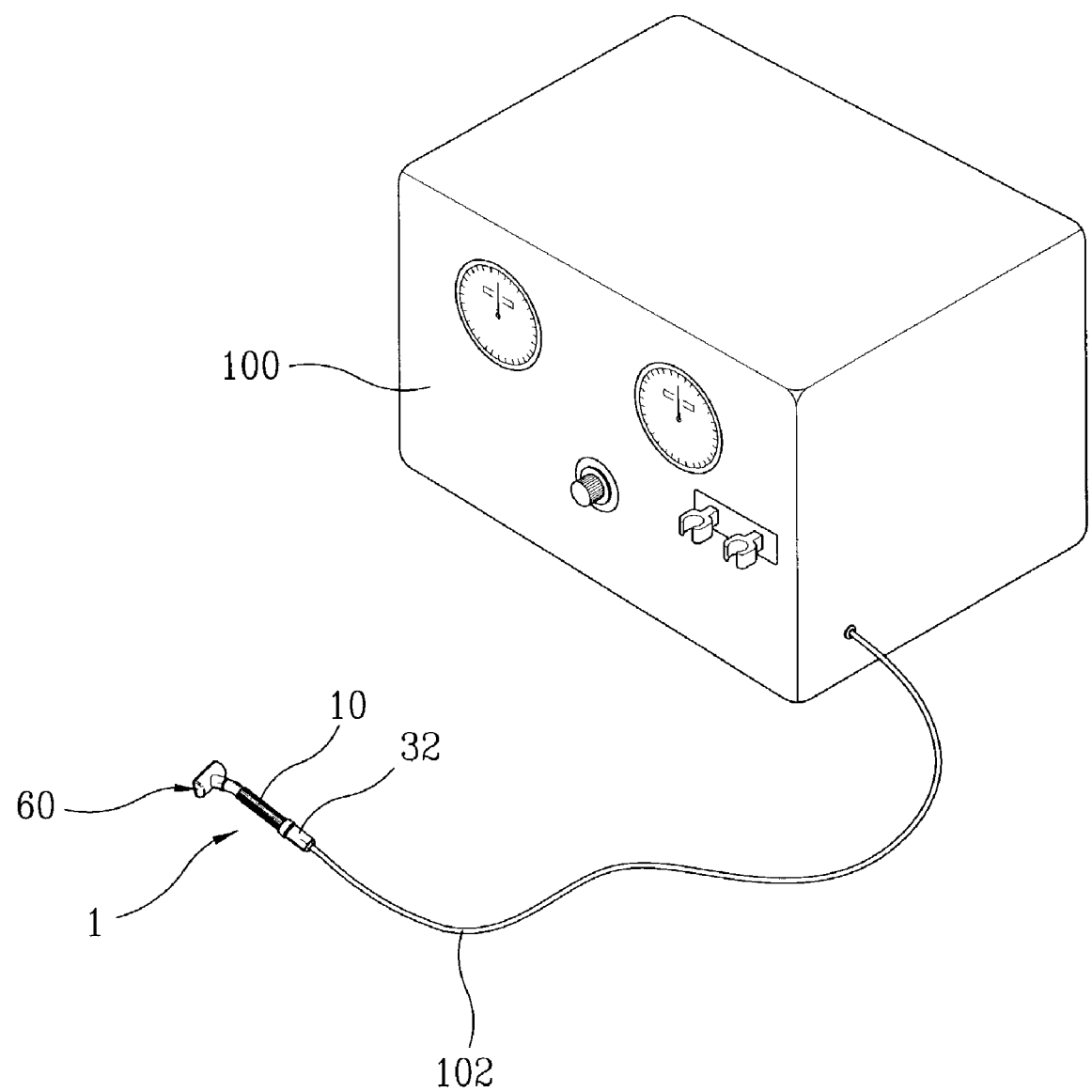
FIG. 6 is the view of the hand piece and the vacuum suction of this invention put together.

FIG. 1 is the perspective view of this invention being properly used; FIG. 2 is the exploded perspective view of the hand piece of this invention being properly used; FIG. 3 is the assembled cross section of this invention being properly used; and FIG. 6 is the view of this invention being in actual use. Drawing sign 1 is the hand piece, the callus remover that connects to the vacuum suction device 100.

The lower part of the main body 10 of the hand piece 1 is bent at a certain degree approximately a quarter of the way up from the bottom, and multiple O rings 24 are inserted from below the bend. That is where the cutter 60 is mounted 20.

In addition, above the above-mentioned main body 10 there is a fastening part 30 with smooth surface on the outside and screw threads 34 on the inside, and on the outside of the fastening part 30 is the holder 32 that can hang on the hook installed on the vacuum suction device, and the suction connector 40, consisting of a faster 42 and a nipple 44, will be screwed into the screw thread 34 of the above-mentioned fastening part 30.

On the other hand, as shown in FIG. 2, the cutter 60 is designed in various shapes such as a "T" shape or an "I" shape for ease of use. You can choose an appropriate cutter 60, and insert it in the mount in the lower part of the main body 10. There are multiple connectors 40 with nipples 44 of varying diameters that go on to the top part of the main body 10, so you can choose one that fits the suction tube 102 of the vacuum suction device 100.

To give a more detailed description of the hand piece 1 we invented, the mount 20 on the main body 10 of the hand piece 1 has surrounding grooves 22 for O rings 24, and the above-mentioned mount 20 is bent at a certain degree.

The mount 20, bent at a certain degree, accommodates cutters 60 of various shapes that have a cutting surface 63 with minute diamond embossments at the bottom (the surface that comes in contact with the skin). The above-mentioned O ring 24 holds the cutter 60 tightly in place, and maintains airtightness.

Above the main body 10 the fastening part 30 is extended for a certain length, and the holder 32 goes around the outside of the fastening part 30, making it possible to hang the hand piece 1 on the hook of the vacuum suction device 100.

Besides, inside the end of the fastening part 30 is a screw thread 34. The connector 40, consisting of the fastener 42 and the nipple 44, is screwed into the screw thread 34. There are multiple connectors 40 with nipples 44 of varying diameters that go on to the top part of the main body 10, enabling you to connect it to any suction tube 102, with varying diameters, of the vacuum suction device 100.

To use the hand piece 1 of this invention, as illustrated in FIG. 2 or 3, choose a cutter 60 with a shape appropriate for callus removal, and connect it to the mount 20 in the lower part of the main body 10.

The nipple 44 of the suction connector 40 fastened to the top part of the main body 10 is inserted into the suction tube 102 installed on the existing vacuum suction device 100 as shown in FIG. 6.

At this time, you can choose a connector 40 with a nipple 44 appropriate for the diameter of the suction tube 102.

Hold the handle of the hand piece 1, and let the cutting surface 63 at the bottom of the cutter 60 come in contact with the skin and rub it against the skin. Then, the cutting surface 63 made of diamond removes calluses of the skin, and the removed calluses will be sucked into the vacuum suction device 100 through the suction hole 64 of the cutter 60 and the passage inside the main body 10.

When removing skin calluses, you can use the "T-shaped" cutter 60 with a large cutting surface 63 for large and flat skin areas, whereas small skin areas, you can use the "I-shaped" cutter 60 with a small cutting surface 63. You can choose either one depending on the area you want to remove calluses from.

Meanwhile, FIG. 4a, 4b or 5a, 5b illustrate an exploded perspective view of the cutter ("T-shaped" and "I-shaped") of this invention. This example is very similar to the previous example of this invention being properly used. However, a noticeable feature is that the cutter 60 has a disposable separate fixer 80 that is detachable.

That is, the cutter 60 is equipped with a injection-molded sheet fixer 80 made of synthetic resin that can be can attached and detached at the bottom, and on the bottom surface of the sheet fixer 80 is the sheet insertion groove 84. The diamond sheet 90 with the diamond in the sheet insertion groove 84 is built in.

Therefore, you will need to insert the sheet fixer 80 inside the cutter 60 to use the callus remover, and when done using it, detach only the sheet fixer 80 and replace it with a new sheet fixer 80 that has a diamond sheet 90. Compared to the example given above, you don't have to sterilize and wash the cutter 60, and as it is disposable, you do not have to worry about sanitary issues such as contagious skin diseases.

As illustrated above, according to the example of this invention being properly used, the lower part of the hand piece's main body is bent at a certain degree for greater usability, and below the bend the configuration is such that the cutter is detachable, so you can choose a cutter with a shape you want. Above the main body you can choose to use a suction connector with nipples of different diameters, thus making it usable with the suction tube installed on the existing vacuum suction device and improving economy and usability.

Additionally, another example of this invention being properly used illustrates that the cutter has a detachable injection-molded sheet fixer made of synthetic resin, minimizing incidence of skin diseases and increasing efficiency of callus removal.

What is claimed is:
1. A vacuum skin treating implement, comprising:
   a hollow hand piece having two end portions, one end portion having a fastening part connected to a vacuum line, and the other end portion having a mount being releasably connected with a hollow cutter;

a hollow cutter releasably mounted to the other end portion of the hollow hand piece structured and adapted to come in contact with and rub against the skin;

a holder fastened to the one end of the hollow hand piece to connect a vacuum line thereto; and a connector having a nipple adapted to connect the vacuum line to the hollow hand piece, wherein the hollow hand piece mount has a bend separating it into an unbent portion and a bent portion, the longitudinal axis of the bent portion being at a predetermined angle to the longitudinal axis of the unbent portion, the bend being located relatively close to the end adapted to connect to the hollow cutter, the holder portion of the hollow hand piece accepts connectors that have nipples of various diameters, the holder portion being coupled to the connector, and the mount of the other end portion of the hollow hand piece is adapted to receive a plurality of different hollow cutters.

2. The skin treating implement of claim 1, wherein the hollow cutter comprises a disposable sheet fixer having a diamond sheet.

3. A vacuum skin treating implement, comprising:

a hollow hand piece having two end portions, one end portion having a fastening part connected with a vacuum line via a fastening part, and the other end portion having a mount that is releasably connected with a hollow cutter;

a hollow cutter releasably mounted on the other end of the hollow hand piece that is structured and adapted to come in contact with and rub against the skin;

a holder connecting a vacuum line to the hollow hand piece; and a connector having a nipple that connects the vacuum line to the hollow hand piece, wherein the hollow hand piece mount has a bend separating it into an unbent portion and a bent portion, the longitudinal axis of the bent portion being at a predetermined angle to the longitudinal axis of the unbent portion, the bend being located relatively close to the end adapted to connect to the hollow cutter, the holder portion of the hollow hand piece accepts connectors that have nipples of various diameters, the holder portion being coupled to the connector, and the mount of the other end portion of the hollow hand piece is adapted to receive a plurality of different hollow cutters.

4. A vacuum skin treating implement, comprising:

a hollow hand piece having two end portions, one end portion being fastened to a vacuum line, and the other end portion having a mount releasably connected with a hollow cutter;

a hollow cutter releasably mounted on the other end of the hollow hand piece;

a holder connecting a vacuum line to the hollow hand piece; and a connector having a nipple connecting the vacuum line to the holder, wherein the hollow cutter comprises a disposable sheet fixer having a diamond sheet, the hollow hand piece mount has a bend separating it into an unbent portion and a bent portion, the longitudinal axis of the bent portion of the mount being at a predetermined angle to the longitudinal axis of the unbent portion, the bend being located relatively close to the end adapted to connect to the hollow cutter, the holder portion of the hollow hand piece accepts connectors that have nipples of various diameters, the holder portion being coupled to the connector, and the mount of the other end portion of the hollow hand piece is adapted to receive a plurality of different hollow cutters.

5. The skin treatment device of claim 4, wherein the hollow hand piece has a bend separating it into an unbent portion and a bent portion, the longitudinal axis of the bent portion being at a predetermined angle to the longitudinal axis of the unbent portion, the bend being located relatively close to the end adapted to connect to the hollow cutter.

6. The skin treatment device of claim 4, wherein the other end portion of the hollow hand piece is adapted to connect to a plurality of different hollow cutters, and wherein the one end of the hollow hand piece is adapted to connect to nipples of various diameter.

* * * * *